United States Patent [19]

Hawkridge et al.

[11] 4,144,143
[45] Mar. 13, 1979

[54] ELECTROLYTIC PRODUCTION OF STABLE METHYL VIOLOGEN FILM

[75] Inventors: Fredrick M. Hawkridge, Richmond, Va.; Harlie L. Landrum, Hattiesburg, Miss.

[73] Assignee: Virginia Commonwealth University, Richmond, Va.

[21] Appl. No.: 845,067

[22] Filed: Oct. 25, 1977

[51] Int. Cl.$^2$ .................. C25D 13/00; C25B 3/00; G01N 27/00
[52] U.S. Cl. .................................. 204/72; 204/74; 204/195 B; 204/195 M; 204/299 EC
[58] Field of Search ............ 204/72, 73 R, 74, 195 B, 204/195 M, 299 EC

[56] References Cited
PUBLICATIONS van Dam et al., J. Electrochem. Soc., vol. 121, pp. 1555–1558, 12/74.

Jasinski, J. Electrochem. Soc., vol. 124, pp. 637–641, 5/77.

Primary Examiner—F.C. Edmundson
Attorney, Agent, or Firm—Barry S. Bissell; Kenneth E. Shaweker; Thomas W. Winland

[57] ABSTRACT

A stable, apparently polymeric, form of 1,1′-dimethyl-4,4′-dipyridyl dichloride is non-reversibly produced on a solid, minigrid electrode surface by means of electrolysis of a solution of the dicationic species using a negative applied potential in the range where the cation radical is heterogeneously formed but not negative enough to produce the neutral species. For example, a thin film is formed on a gold electrode at a potential of between about −0.750 V and −0.950 V vs a Ag/AgCl reference electrode.

The electrode and stable surface films are electro-active in heterogeneous reduction and oxidation of large biological molecules, making the modified electrode useful, for example, in the quantitative analysis of heme proteins in biological fluids (blood, urine).

6 Claims, No Drawings

ELECTROLYTIC PRODUCTION OF STABLE METHYL VIOLOGEN FILM

BACKGROUND OF THE INVENTION

Various bipyridinium salts and polymers which undergo reversible oxidation-reduction (redox) changes in spectral absorption characteristics are known and described in the art. Specifically, these compounds have been used as mediators in electro-chemical reduction and oxidation of biological molecules.

The 4,4'-bipyridinium unit is commonly known as a "viologen" and it undergoes two separate one-electron reduction steps from the dication to the cation to the neutral (dihydrobipyridyl) species as shown, for example, in U.S. Pat. No. 3,856,714, which is incorporated herein by reference. The dicationic and neutral forms are colorless, but the cationic form is a deep blue-violet color. This property has resulted in the use of such viologens as photochemical or redox indicators and as the visual element in alphanumeric image displays.

Polymers containing repeating viologen units have been previously described in the art but have been produced by alkylation or interfacial polycondensation. See U.S. Pat. Nos. 3,641,034; 3,671,250; 3,694,384; and 3,856,714.

Several prior patents describe the electrolytic polymerization of monomers of viologens or similar compounds. For example, U.S. Pat. No. 3,574,072 describes generally the polymerization of numerous heterocyclic compounds.

U.S. Pat. No. 3,854,794 discloses the use of viologens in image display cells wherein a film of the cation radical salt (not a polymer) is produced on a cathode at rather high potentials. The film deposition process is described as being reversible by reversing the electrode polarity. A literature article in the Journal of the Electrochemical Society (Vol. 124, No. 5, May 1977, p. 637) discloses additional insoluble, heptyl viologen compounds for image displays.

In the oxidation and reduction of biological molecules it is usually found that solid metal electrodes are not capable of directly transferring electrons at a high rate. Viologens may therefore be used as mediators to intermediate the transfer of electrons from the electrode to the molecule. Unfortunately, the mediators tend to hamper optical studies of the redox reactions due to their large absorbances and electron paramagnetic resonance signals.

SUMMARY OF THE INVENTION

It is an object of the present invention to provide an electrolytic method for forming a stable film of a particular viologen compound.

It is also an object of the present invention to produce an electroactive element, modified on the surface with the particular stable viologen compound, which is useful in redox reactions with large biological molecules resulting in a tool for the quantitative determination of specific biological molecules in solution.

It is further an object to provide a method for rapid redox reactions of biological molecules without mediators which hinder accurate quantitative assay.

In accordance with the objectives, the invention is a method, and the electroactive element produced thereby, for nonreversibly depositing a stable film of 1,1'-dimethyl-4,4'-dipyridyl dichloride (commonly known as methyl viologen) on a solid electrode, and, in particular, on a minigrid electrode having qualities hereafter described. The electroactive element is capable of transferring electrons with biological molecules (such as heme proteins, spinach ferrodoxin, and the components of the mammalian oxidative phosphorylation sequence) with or without applying a potential to the element. The element can transfer electrons without an applied potential if a charge is stored therein by applying a negative potential before disconnecting the potential source and contacting the biological solution.

The inventive method for electrochemical production of the surface film comprises introducing a solid conductive substrate, preferably a minigrid electrode of gold, into an electrolysis cell as one electrode thereof, introducing an electrolyte solution comprising dication molecules of 1,1'-dimethyl 4,4'-dipyridyl dichloride into the electrolysis cell and in contact with the solid conductive substrate, and subjecting the electrolyte solution to electrolysis and forming the stable film by applying a potential in the range of potentials between the formal potential of the first reduction step (of the dication unit to the cation unit) and the formal potential of the second reduction step (of the cation unit to the neutral unit). The stable film is believed to be a polymeric form of methyl viologen.

The solid conducting substrate preferably comprises gold and is a minigrid sheet having a semitransparent, screenlike appearance formed of fine, intersecting wires. The solid electrode or wire surface is preferably rough with a crystalline texture which appears to favor deposition of the stable film. A light transmission through the minigrid of at least about 40% (between 40 and 90 percent) is preferred to enable optical analysis and adequate surface area for deposition.

DESCRIPTION OF THE INVENTION

Spectropotentiostatic and other techniques for quantitative determination of heme proteins in body fluids exist in the art. The present invention intends to improve these techniques by providing an electroactive element which has the ability of rapidly transferring electrons with large biological molecules and, therefore, the ability to poise the redox potential of a sample and allow the sequential reduction of each heme protein, such as hemoglobin and myoglobin, in the sample.

Metal electrodes in the past have been found to heterogeneously transfer electrons to large biological molecules too slowly to be of use in such direct reductions. The present invention provides a method of modifying the prior electrodes to drastically increase their ability to transfer electrons and their utility and efficiency as a tool in quantitative techniques of analysis.

The invention will be more clearly understood when considering the following examples.

EXAMPLE 1

Preparation of the Electroactive Element

An optically-transparent, thin-layer electrolysis cell (OTTLE cell) such as shown in an article by Norris, et al. (*Analytical Chemistry*, [48] p. 630, 1976) was used in the following examples. The latter article is incorporated herein by reference in order to provide more information about the cell. Essentially, the cell is a normal electrolytic cell, but which allows the use of very small amounts of electrolyte. The cell has a gold minigrid electrode, an auxiliary electrode (which can also be a minigrid) and a reference electrode. The reference electrode in the following examples was Ag/AgCl.

The gold minigrid sheet is a very thin, semitransparent screen (about 60% transmittance) which can be commercially acquired from Buckbee-Mears, St. Paul, Minn., USA, in several sizes. The present inventor has used a screen with 120 wires per inch; however, others are available and are useful. The minigrids are apparently fabricated using an electrolytic deposition of gold onto a grid-like mandrel which results in a rough crystalline appearance on a "U" shaped cross section of the wires which is particularly useful in the present invention. On the contrary, thin sheet electrodes of gold, made by a rolling process, exhibit a smooth surface appearance which were found not to result in as good a deposition of polymer film as did the minigrids.

In producing the polymer film, electrolyte solution at pH 7 of 1 millimolar methyl viologen, 0.1 molar phosphate buffer and 0.1 molar NaCl was placed in an OTTLE cell using the gold minigrid as both electrodes. A potential of about −0.920 V was applied for 10 minutes and resulted in an amorphous film on the minigrid surface. Tests were performed to substantiate that a methyl viologen polymeric film is formed and to eliminate other possible species such as the salts of the cation radical of methyl viologen. The tests seemed to indicate that the film could be polymeric.

The film was stable on the surface with respect to the application of a potential of between +0.500 V to −0.950 V, to reaction with molecular oxygen, to reaction with the dication of methyl viologen and to reaction with Fe (III). Moreover, once the film was formed in the cell, the neutral unit of methyl viologen could not be electrochemically produced therein.

EXAMPLE 2

REDUCTION OF SPINACH FERREDOXIN

The surface modified gold minigrid element produced in Example 1 was washed with distilled water and placed in the OTTLE cell with an electrolyte solution consisting of 0.30 millimolar spinach ferredoxin in a buffer medium of 0.1 M tris, 0.1 M NaCl at pH 7.1. A cyclic voltammogram was run which indicated that the location of the peak for heterogeneous reduction of the species agreed with the known formal potential of ferredoxin, −0.428 vs NHE. The cell was further mounted in a spectrometer and spectropotentiostatic experiments were performed monitoring the change in absorbance at 420 nanometers versus time. The results indicated a significant rate of electron transfer between the surface modified gold minigrid element and the ferredoxin. Similar experiments using a gold element without the surface film modification indicated that the time needed for reduction of ferredoxin was at least an order of magnitude larger than for the surface modified gold element.

A Hg/Au amalgam minigrid electrode was made from a gold minigrid and then used as in Example 1 to produce an electroactive element. The deposit was not as good as the gold by itself. The formal potential range between the first and second reductions was found to be −0.850 V to 0.980 V. A stable film was produced using these parameters.

The potential range for the gold minigrid was determined by measuring the formal potentials for the first and second reduction steps of the dication of methyl viologen under the conditions specified in Example 1. The first formal potential was determined to be −0.750 V and the second potential was −0.950 V on gold.

The minigrid electrode may be fabricated of other materials such as nickel, copper or platinum, whereupon the formal potentials for the first and second reduction would vary somewhat. These materials are not expected to be as useful as gold in the present method and gold is the preferred minigrid material.

Concentrations of methyl viologen in the electrolyte may range an order of magnitude from that used in Example 1. The concentration does not appear critical to obtaining a good deposit and experiments have been successfully run with from 0.1 millimolar to 10 millimolar. The buffer concentration is also not ciritcal although the pH should be in the range of about 5–9, preferably about 7. Formal potentials for the first and second reductions will vary somewhat depending on these conditions, but can be easily determined by those skilled in the art.

Although concentrations are not critical to obtaining a stable deposit according to the invention, it has been found that it is preferable to form a thick film by sequentially exhausting several 1 millimolar methyl viologen solutions rather than continuously depositing a more concentrated (for example, 10 millimolar) solution. In fact, if a 1 millimolar methyl viologen solution is electrolyzed, replaced with a fresh, second 1 millimolar solution which is electrolyzed and replaced with third, fourth, and fifth fresh electrolytes, the rate of deposit on the minigrid is greater for each successive solution than the preceding solution until the fifth is reached. The reason for this is not clearly understood but may also relate to the surface characteristics of the previous deposit.

A clinical method for determining the concentrations of the heme proteins, myoglobin and hemoglobin, in a blood sample using the electroactive element produced according to the invention could be as follows.

The formal potentials for the myoglobin and hemoglobin molecules are 0.046 V and 0.144 V vs NHE, respectively. The first absorption spectrum would be recorded with an applied potential sufficiently positive of both formal potentials (e.g., 0.300 V vs NHE) so that both molecules will be quantitatively oxidized. The potential would then be changed to a value between both formal potentials (e.g., 0.095 V vs NHE) where the ratio of the oxidized to reduced concentrations of the two molecules would be known from the Nernst equation. The absorption spectrum would be recorded again at this applied potential. Finally, a potential sufficiently negative to quantitatively reduce both molecules would be applied and the spectrum recorded. A simple simultaneous equations calculation would give the concentration of each component.

A proposed method would use the electroactive element in an amperometric detector cell coupled to a high performance liquid chromatograph column. The different heme proteins would be separated based on the difference in elution times and then amperometrically detected by the electroactive element of the invention.

We claim:

1. A method for the non-reversible electrochemical production of a stable film of 1,1′-dimethyl-4,4′-dipyridyl dichloride which is stable against a positive applied potential in an electrolytic cell and which comprises (a) introducing an electrode comprising a plurality of wires forming a minigrid sheet into an electrolytic cell as one electrode thereof, said wires being formed by electrolytic deposition of a metal selected from the group consisting of gold, platinum, copper, nickel, a mercury/gold amalgam and alloys thereof;

(b) introducing an electrolyte solution having a pH of about 5-9 comprising dication molecules of 1,1'-dimethyl-4,4'-dipyridyl dichloride at a concentration of up to 10 millimolar into the electrolytic cell and into contact with the minigrid electrode; and (c) subjecting the electrolyte solution to electrolysis and irreversibly forming the stable film by temporarily applying a potential in the range between the formal potential of the first reduction step of the dication molecules and the formal potential of the second reduction step of the dication molecules.

2. The method of claim 1 wherein the metal selected for the minigrid electrode is gold.

3. The method of claim 1 wherein the minigrid electrode is made of intersecting wires and the minigrid has a light transmittance of at least 40%.

4. An electroactive element for the direct electrochemical oxidation or reduction of biological molecules comprising a solid, electrically conductive substrate and a stable film thereon of a form of 1,1'-dimethyl-4,4'-dipyridyl dichloride and wherein the element is made by the steps comprising (a) introducing an electrode comprising a plurality of wires forming a minigrid sheet into an electrolytic cell as one electrode thereof, said wires being formed by electrolytic deposition of a metal selected from the group consisting of gold, platinum, copper, nickel, a mercury/gold amalgam and alloys thereof;

(b) introducing an electrolyte solution having a pH of about 5-9 comprising dication molecules of 1,1'-dimethyl-4,4'-dipyridyl dichloride at a concentration of up to 10 millimolar into the electrolytic cell and into contact with the minigrid electrode; and (c) subjecting the electrolyte solution to electrolysis and irreversibly forming the stable film by temporarily applying a potential in the range between the formal potential of the first reduction step of the dication molecules and the formal potential of the second reduction step of the dication molecules.

5. The method of claim 4 wherein the metal selected for the minigrid electrode is gold.

6. The method of claim 4 wherein the minigrid electrode is made of intersecting wires and the minigrid has a light transmittance of at least 40%.

* * * * *